US008634918B2

(12) United States Patent
Chambers

(10) Patent No.: US 8,634,918 B2
(45) Date of Patent: Jan. 21, 2014

(54) MEDICAL IMPLANT WITH SAFETY FEATURE

(75) Inventor: John Chambers, Mona Vale (AU)

(73) Assignee: Cochlear Limited, Macquarle University, NSW (AU)

( * ) Notice: Subject to any disclaimer, the term of this patent is extended or adjusted under 35 U.S.C. 154(b) by 0 days.

(21) Appl. No.: 13/123,684

(22) PCT Filed: Oct. 9, 2009

(86) PCT No.: PCT/AU2009/001344
§ 371 (c)(1),
(2), (4) Date: Sep. 22, 2011

(87) PCT Pub. No.: WO2010/040189
PCT Pub. Date: Apr. 15, 2010

(65) Prior Publication Data
US 2012/0010476 A1    Jan. 12, 2012

(30) Foreign Application Priority Data

Oct. 9, 2008  (AU) ................................ 2008905254
Apr. 28, 2009 (AU) ................................ 2009901836

(51) Int. Cl.
*A61N 1/08*  (2006.01)
(52) U.S. Cl.
USPC ................................ 607/36; 607/57; 607/137
(58) Field of Classification Search
None
See application file for complete search history.

(56) References Cited

U.S. PATENT DOCUMENTS

| 5,606,264 | A | | 2/1997 | Licari et al. |
| 5,837,935 | A | * | 11/1998 | Carper et al. .............. 174/50.51 |
| 6,358,281 | B1 | | 3/2002 | Berrang et al. |
| 6,411,854 | B1 | * | 6/2002 | Tziviskos et al. .............. 607/57 |
| 6,550,306 | B1 | * | 4/2003 | Bensley ........................ 73/12.04 |
| 7,447,533 | B1 | * | 11/2008 | Fang et al. ..................... 600/310 |
| 7,601,537 | B2 | * | 10/2009 | Gueissaz et al. .................. 436/3 |
| 2002/0019669 | A1 | | 2/2002 | Berrang et al. |
| 2003/0171787 | A1 | | 9/2003 | Money et al. |
| 2003/0183001 | A1 | * | 10/2003 | Zimmermann et al. ........ 73/295 |
| 2004/0124082 | A1 | * | 7/2004 | Nakagawa ..................... 204/424 |
| 2007/0255352 | A1 | | 11/2007 | Roline et al. |
| 2008/0046018 | A1 | | 2/2008 | Von Huben et al. |

FOREIGN PATENT DOCUMENTS

| WO | WO-97/01314 | | 1/1997 |
| WO | WO 2005049482 A1 | * | 6/2005 |

OTHER PUBLICATIONS

International Search Report for PCT/AU2009/001344, mailed Dec. 17, 2009, 5 pages.
Written Opinion for PCT/AU2009/001344, mailed Dec. 17, 2009, 7 pages.

* cited by examiner

*Primary Examiner* — Brian T Gedeon
*Assistant Examiner* — Ankit Tejani
(74) *Attorney, Agent, or Firm* — Kilpatrick, Townsend & Stockton, LLP.

(57) ABSTRACT

A medical implant, comprising: a hermetically sealed housing; and a hermeticity failure sensor configured to detect a failure in the hermeticity of the housing, and, following a failure detection, trigger one or more additional operations.

25 Claims, 14 Drawing Sheets

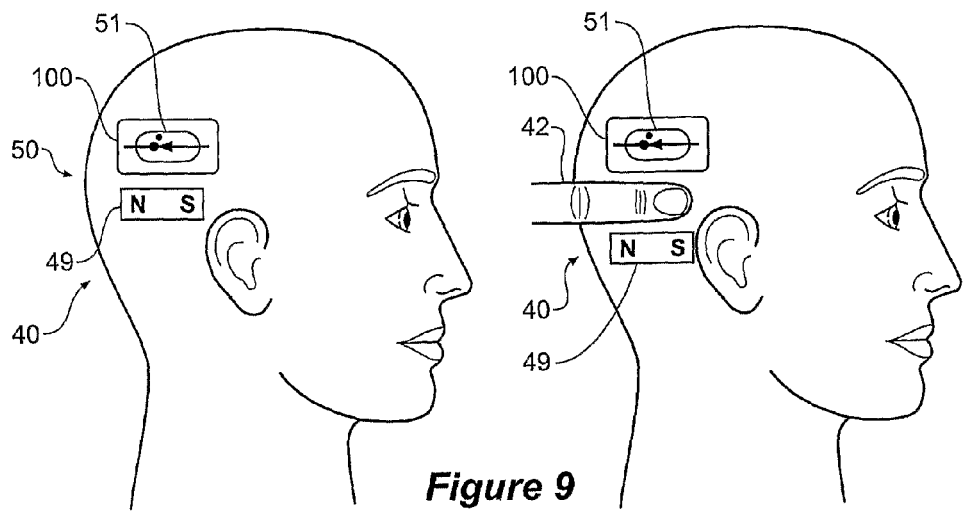
*Figure 9*
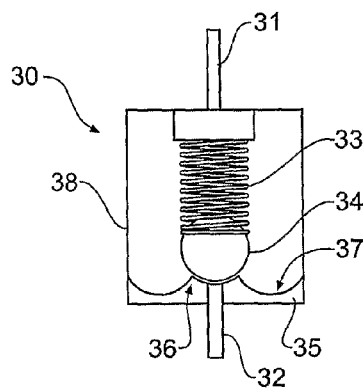   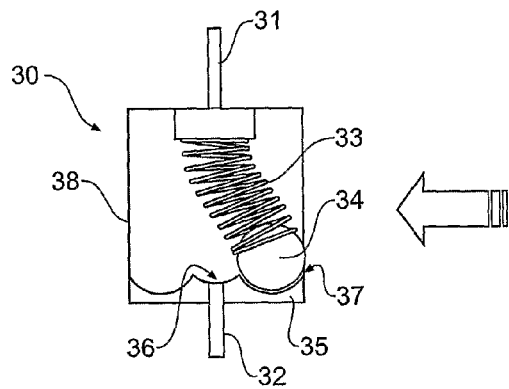
*Figure 10A*   *Figure 10B*
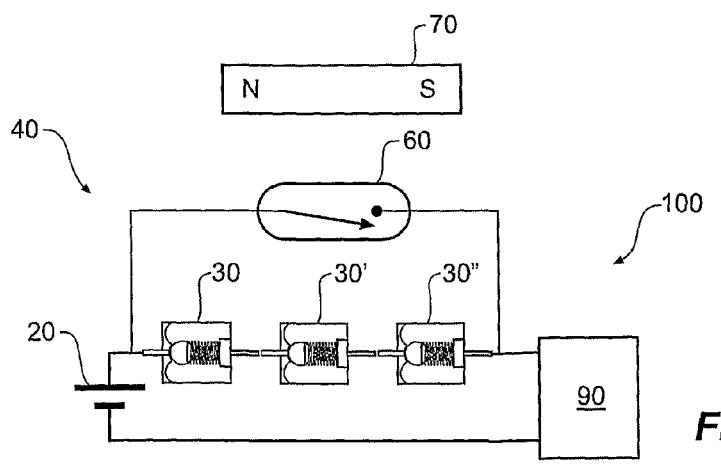
*Figure 11*

MEDICAL IMPLANT WITH SAFETY FEATURE

CROSS-REFERENCE TO RELATED APPLICATIONS

This application is a National Stage application of International Application No. PCT/AU2009/001344, filed Oct. 9, 2009, and claims priority from Australian Provisional Patent Application No. 2008905254, entitled "Power Control For A Medical Implant," filed Oct. 9, 2008, and from Australian Provisional Patent Application No. 2009901836, entitled "Medical Implant With Safety Feature," filed Apr. 28, 2009. The contents of these applications are hereby incorporated by reference herein.

The following documents are referred to in the present application: US Patent Application No. 2003/0171787 entitled "Cochlear Implant"; U.S. Pat. No. 6,358,281 entitled "Totally Implantable Cochlear Prosthesis"; International Patent Application No. PCT/AU96/00403 (WO97/01314) entitled "Apparatus And Method Of Controlling Speech Processors And For Providing Private Data Input Via The Same". The entire content of each of these documents is hereby incorporated by reference.

BACKGROUND

Medical implants are used in a wide variety of applications, from regulating heart rhythm (e.g. a pace maker) to improving hearing in a user or recipient. Implantable hearing prostheses, such cochlear implants, are widely used in restoring a sense of hearing to profoundly deaf persons.

In a cochlear implant, electrical stimulation signals are applied directly to the auditory nerve fibers of the recipient, thereby allowing the brain to perceive a hearing sensation that approximates the natural hearing sensation. More particularly, in operation, audio signals are received via a microphone, and are provided to a sound processing unit. The sound processing unit converts the audio signals into coded signals that are provided to a stimulator unit that uses the coded signals to generate the stimulation signals. The stimulator unit is electrically connected to an electrode array implanted in the recipient's cochlea and that delivers the stimulation signals to the recipient.

In practice, the sound processing unit is generally located externally to the recipient, and the stimulator is implanted within the recipient, usually near the mastoid and underneath the surrounding tissue. The sound processing unit and stimulator unit communicate using various wireless transmission systems, including a radio frequency (RF) link.

There is always some risk of malfunction of cochlear implants and other medical implants. Although these implants are designed to have minimal impact on a recipient's safety should they fail, the outcome of some failure modes is difficult to either control or predict. For example, failure of a random semiconductor component within an implanted device may cause localized unsafe heating of adjacent body tissue and potential recipient discomfort. Additionally, a strong impact to a recipient's head has the potential to damage the hermetic housing of an implant, thereby allowing the ingress of body fluid and egress of potentially harmful chemicals. Furthermore, upon bridging of electrically powered circuitry, the ion rich, aqueous body fluids would be subject to electric current flow, electrolysis and subsequent production of toxic substances. Under the pressure created by the electrolytic evolution of gaseous components, these toxic substances might be expelled into surrounding body tissue with dire effect to the recipient.

SUMMARY

In accordance with one aspect of the present invention, a medical implant is provided. The medical implant comprises: a hermetically sealed housing; and a hermeticity failure sensor configured to detect a failure in the hermeticity of the housing, and, following a failure detection, trigger one or more additional operations.

In accordance with another aspect of the present invention, an operational method of a medical implant having a hermetically sealed housing is provided. The method comprises detecting a failure in the hermeticity of the housing; and triggering, following the failure detection, one or more operations.

DRAWINGS

Embodiments of the present invention are described herein in conjunction with the accompanying drawings, in which.

Figure 3:
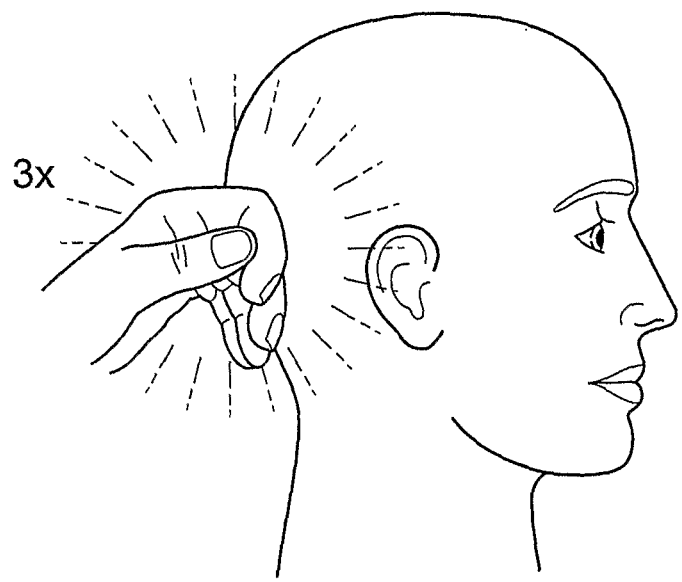
FIG. 3 is a schematic illustration of a power source disconnect event, in accordance with one embodiment of the present invention.
Figure 4:
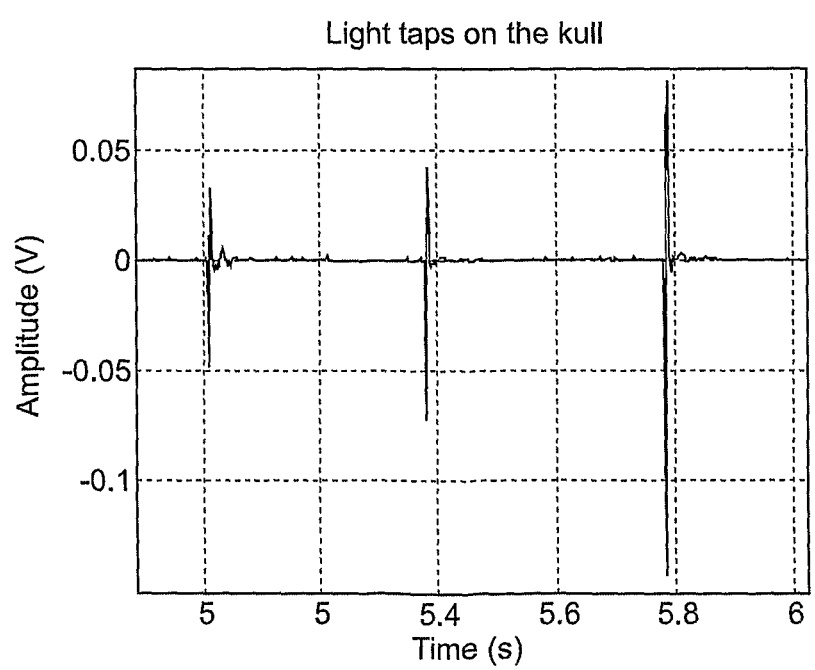
Figure 5:
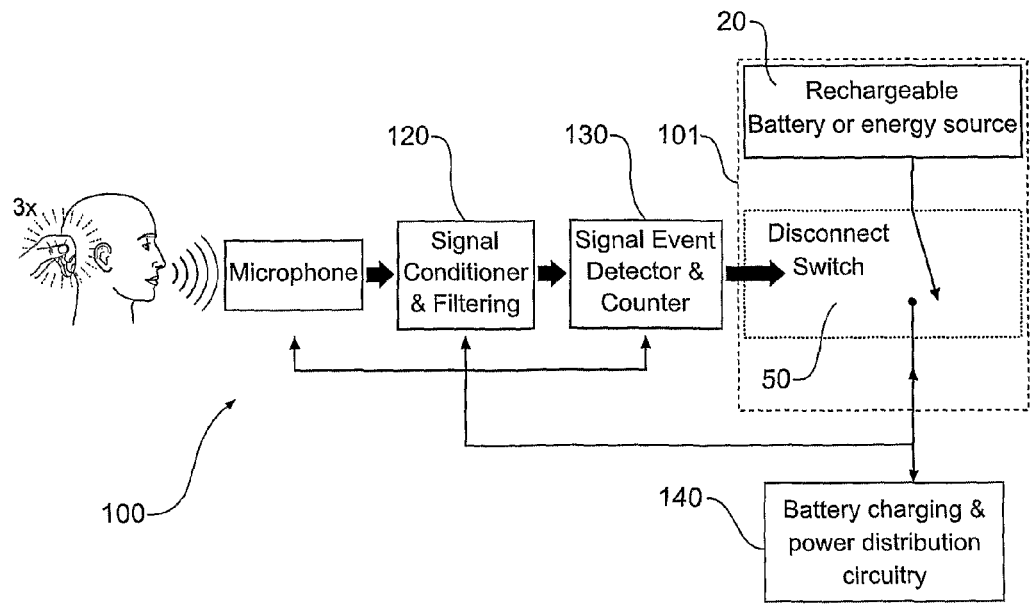
Figure 6:
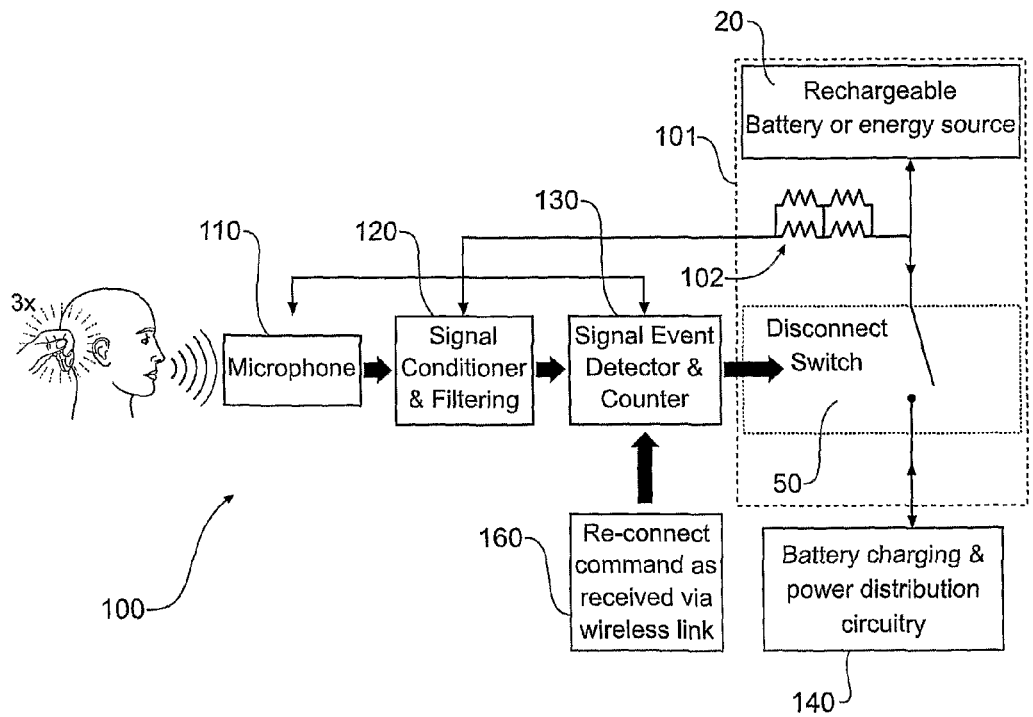
Figure 7:
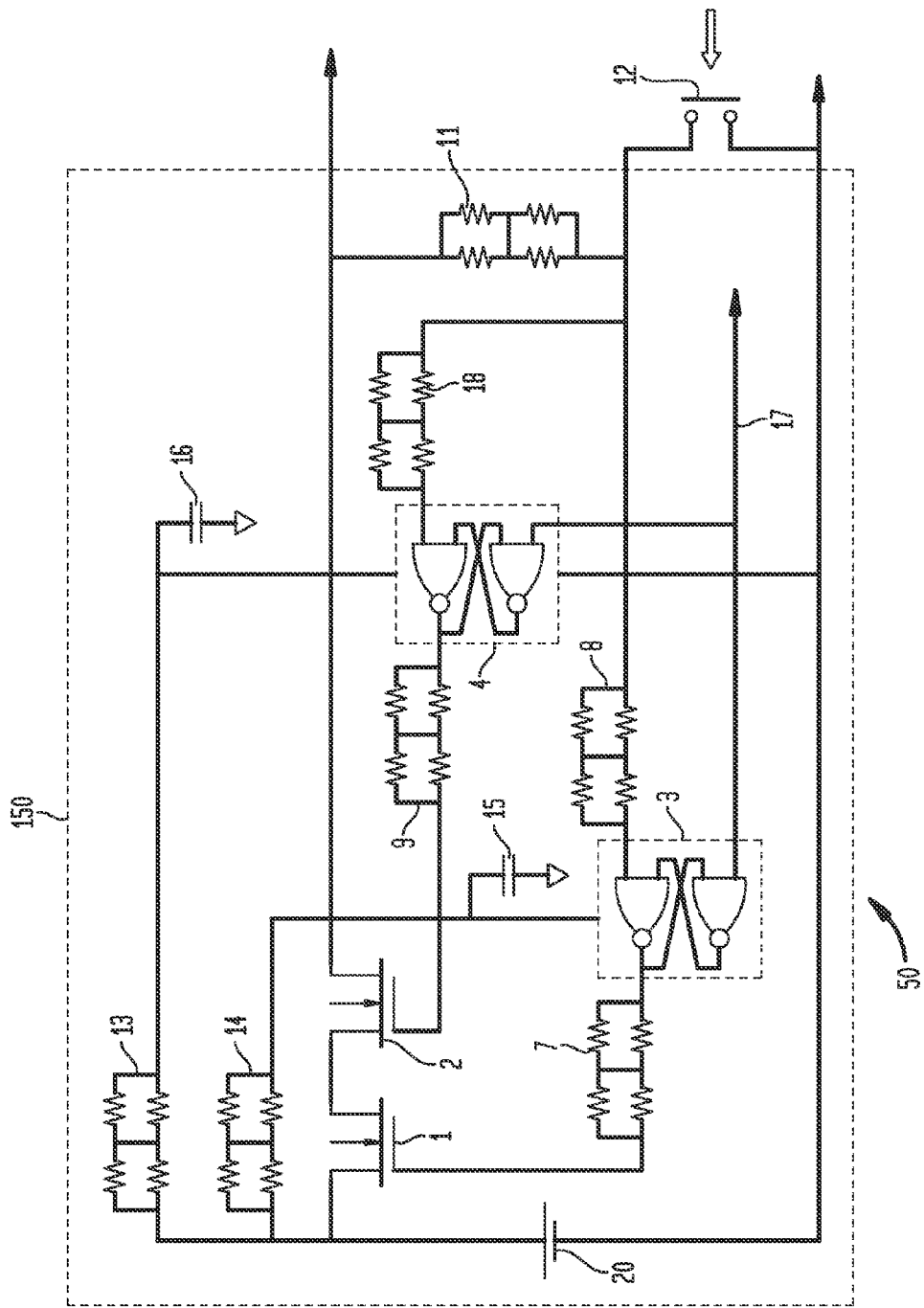
Figure 8:
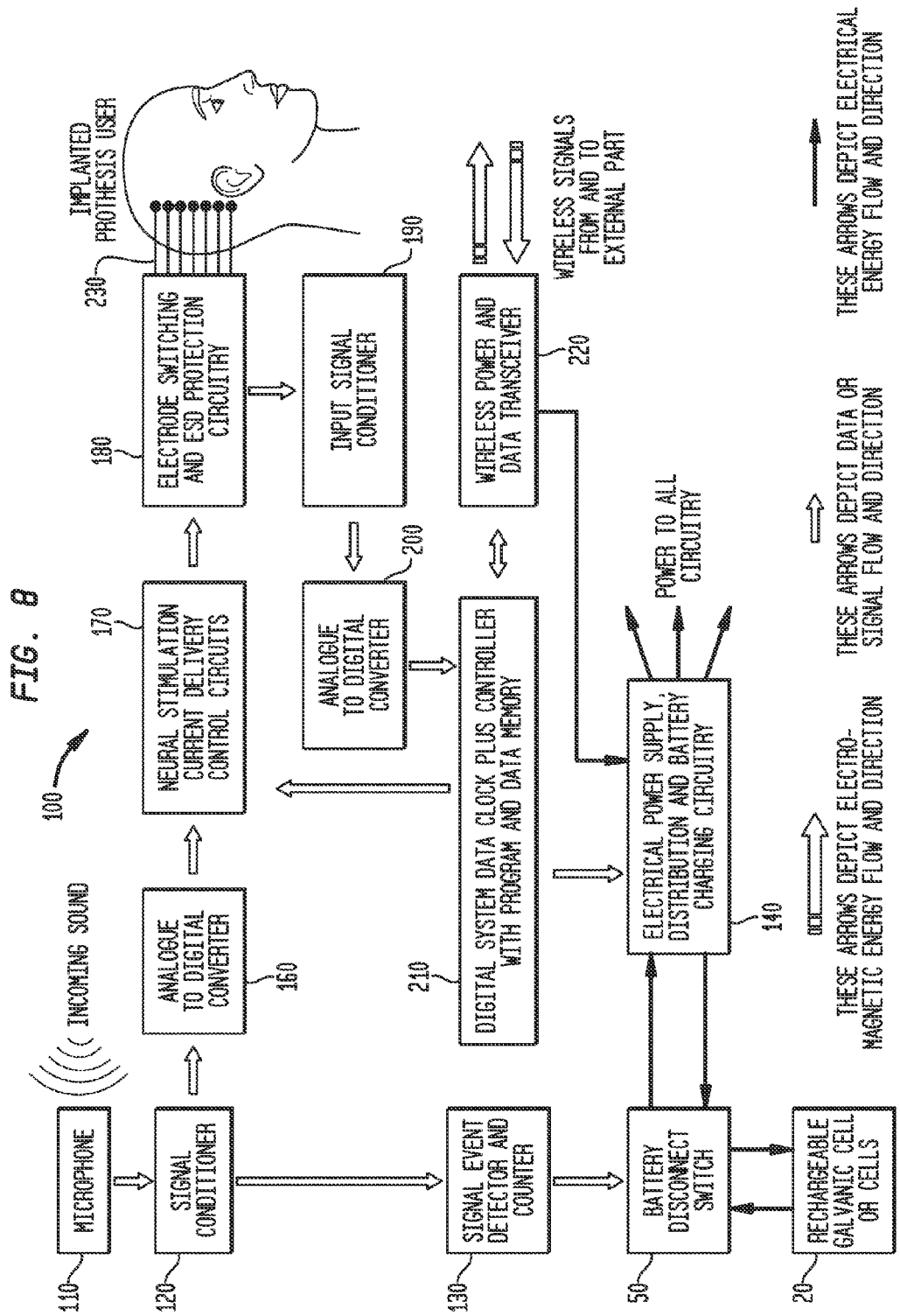
Figure 12:
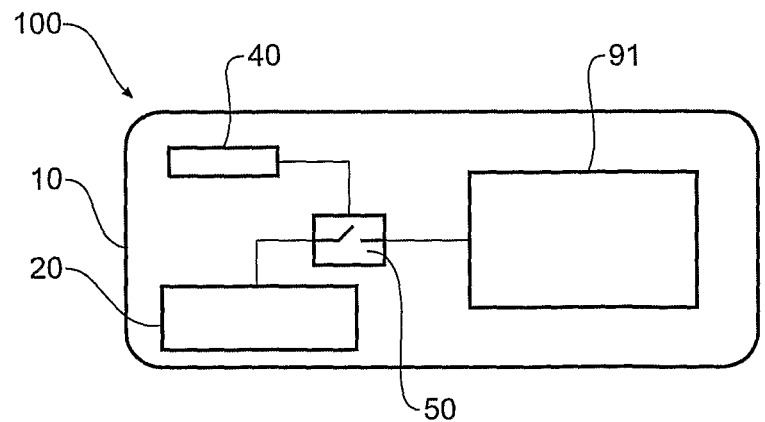
Figure 13:
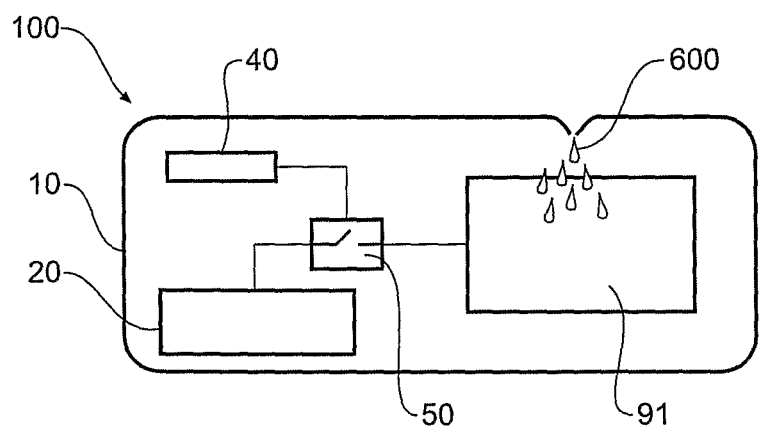
Figure 14:
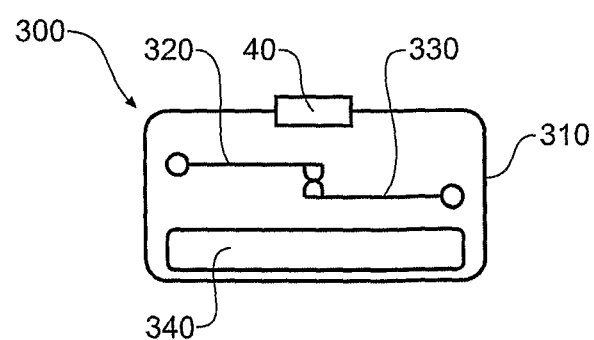
Figure 15:
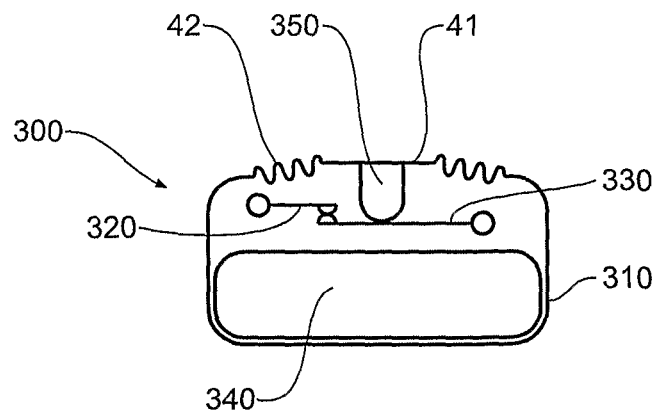
Figure 16A:
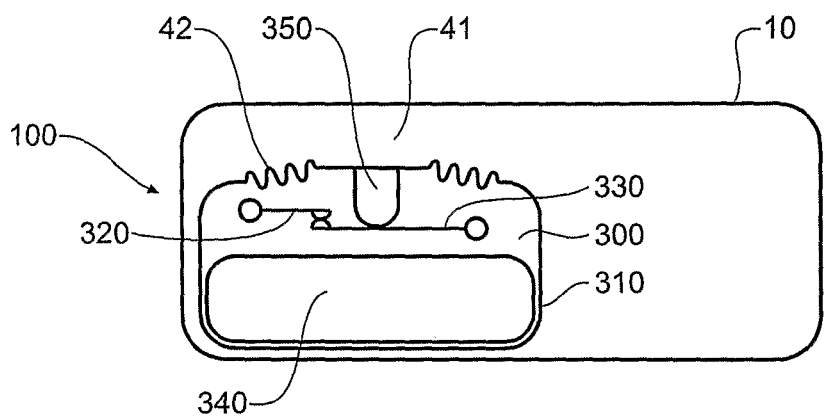
Figure 16B:
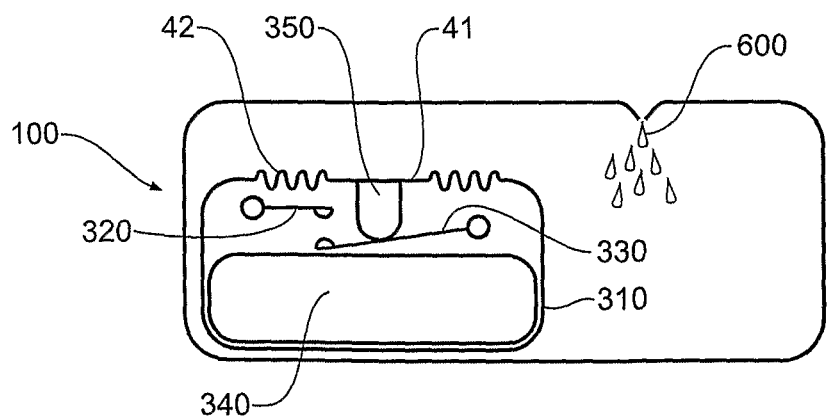
Figure 17A:
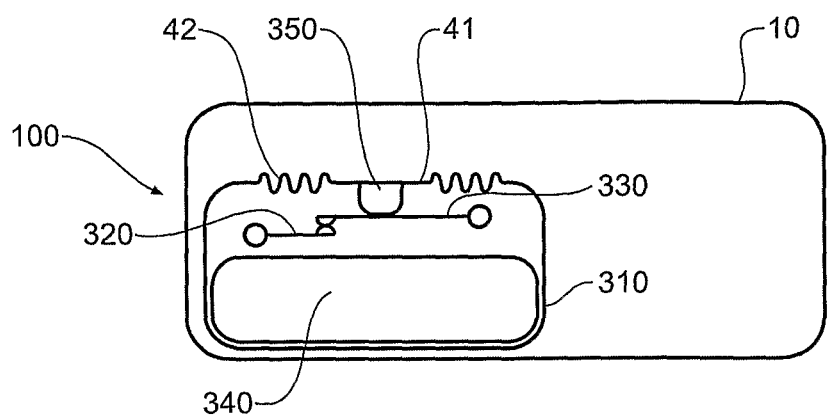
Figure 17B:
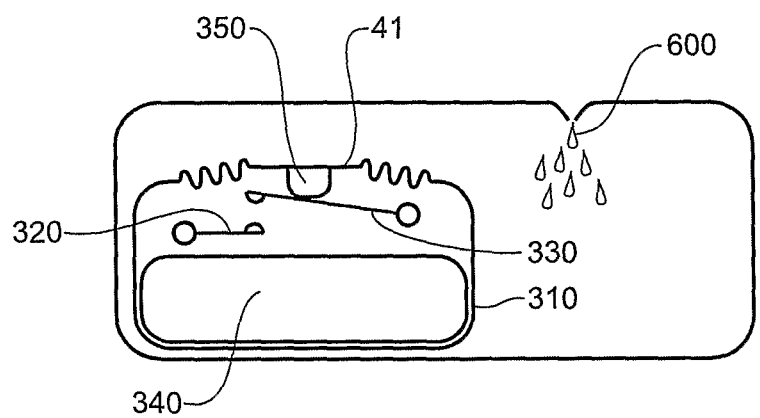
Figure 18A:
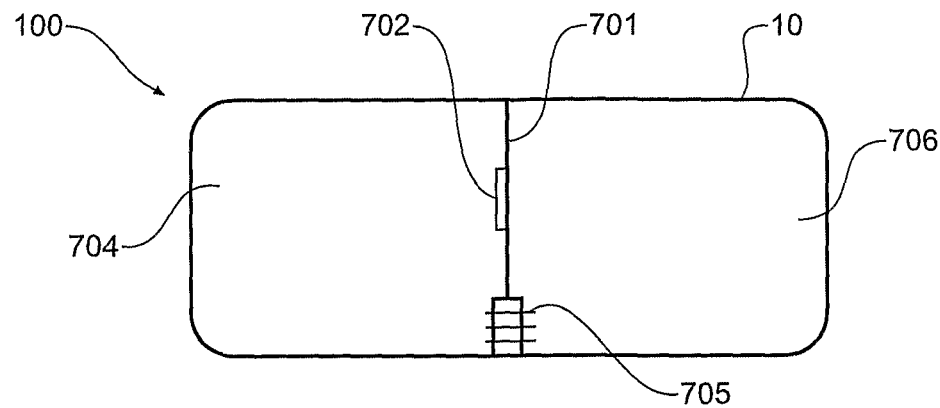
Figure 18B:
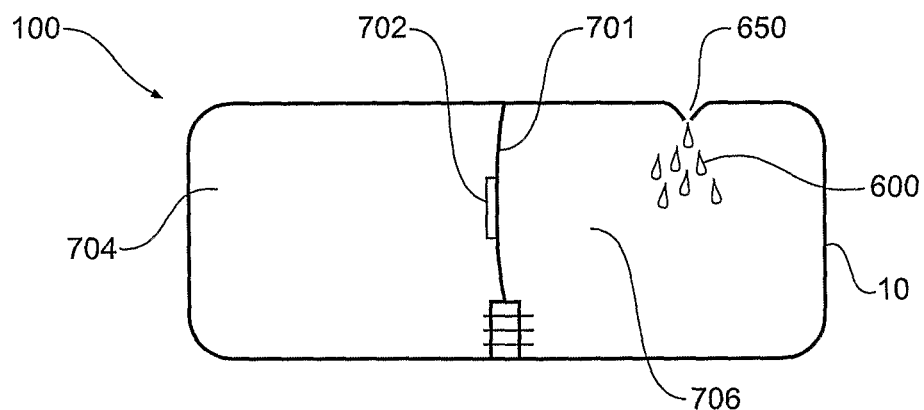
Figure 18C:
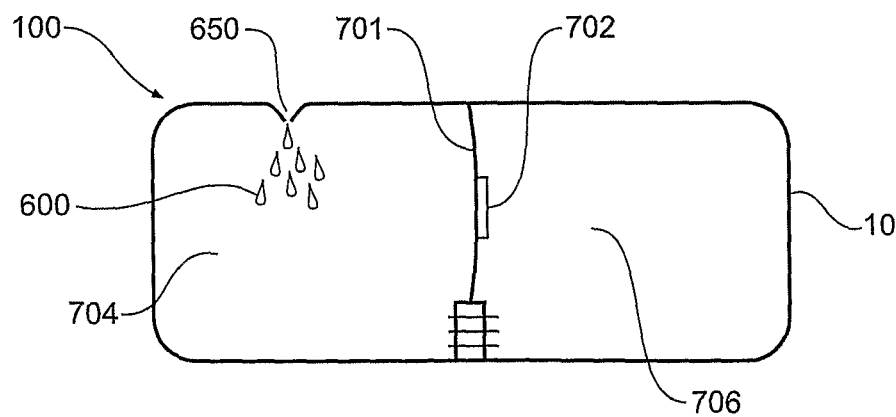
Figure 19A:
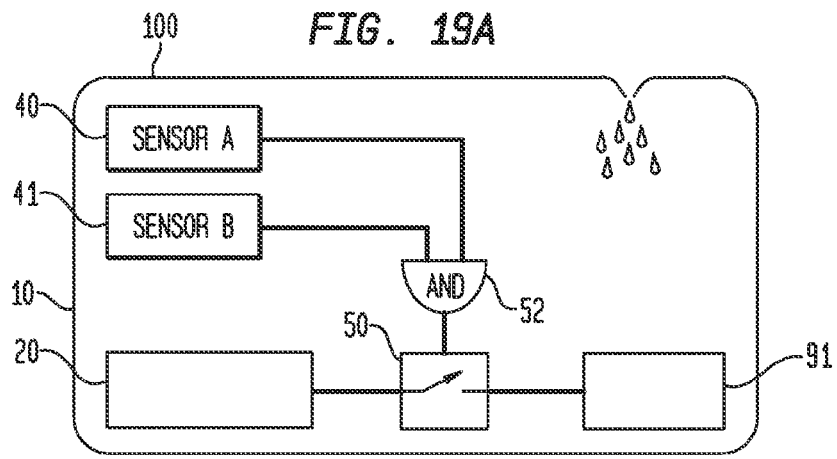
Figure 19B:
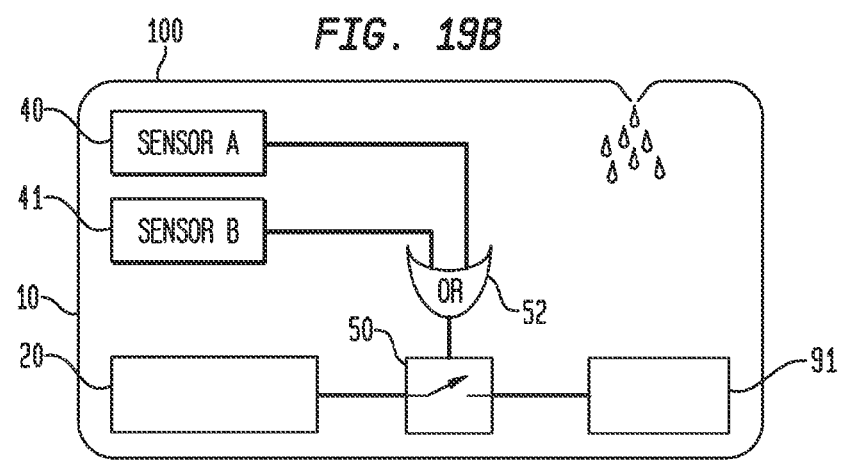
Figure 19C:
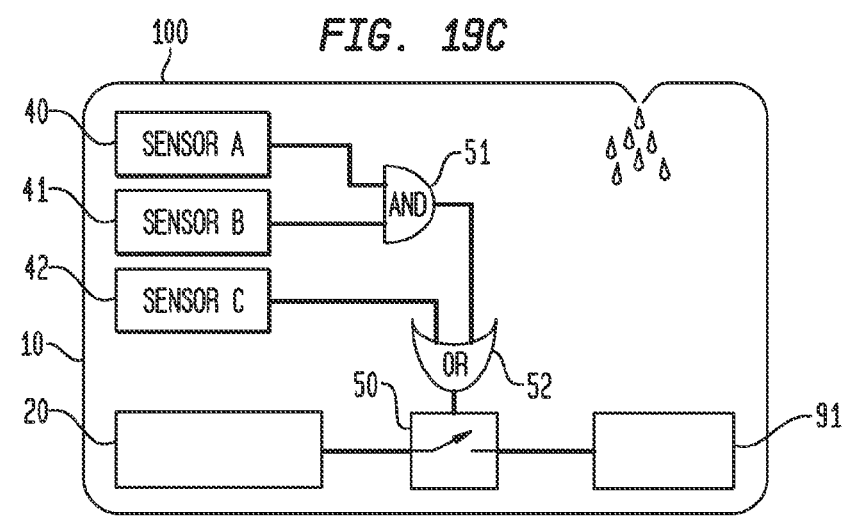
Figure 20:
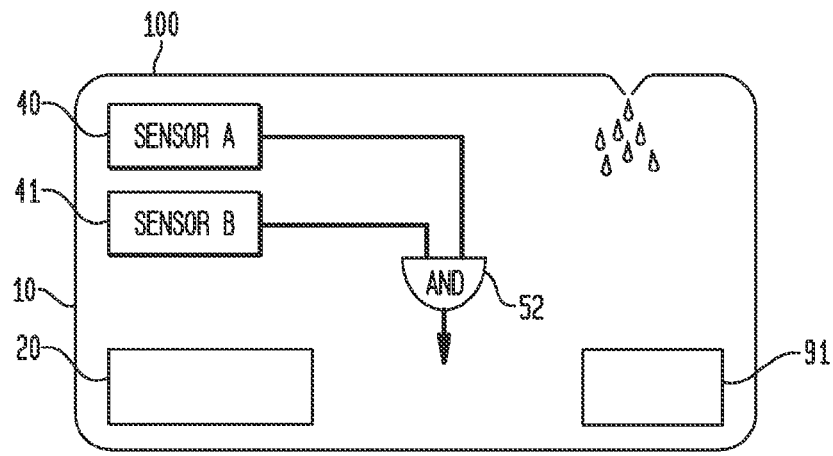
Figure 21:
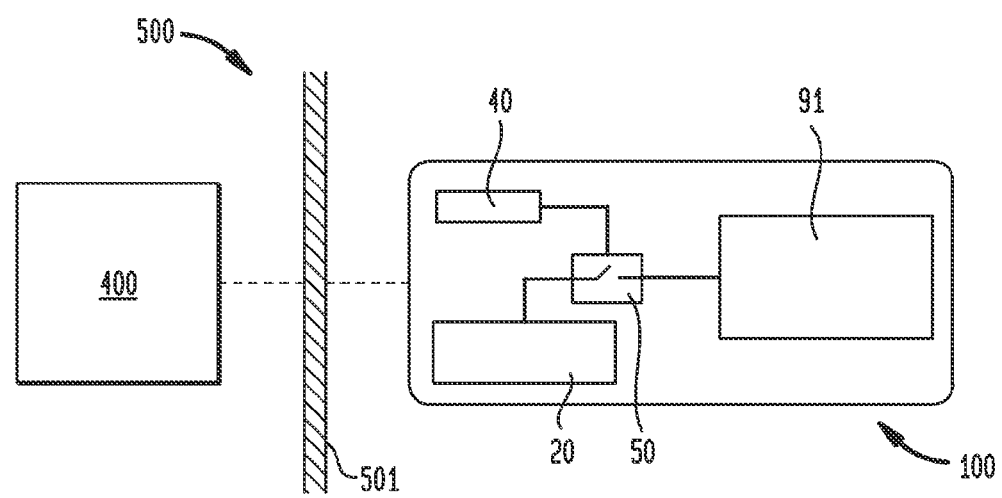
Figure 22:
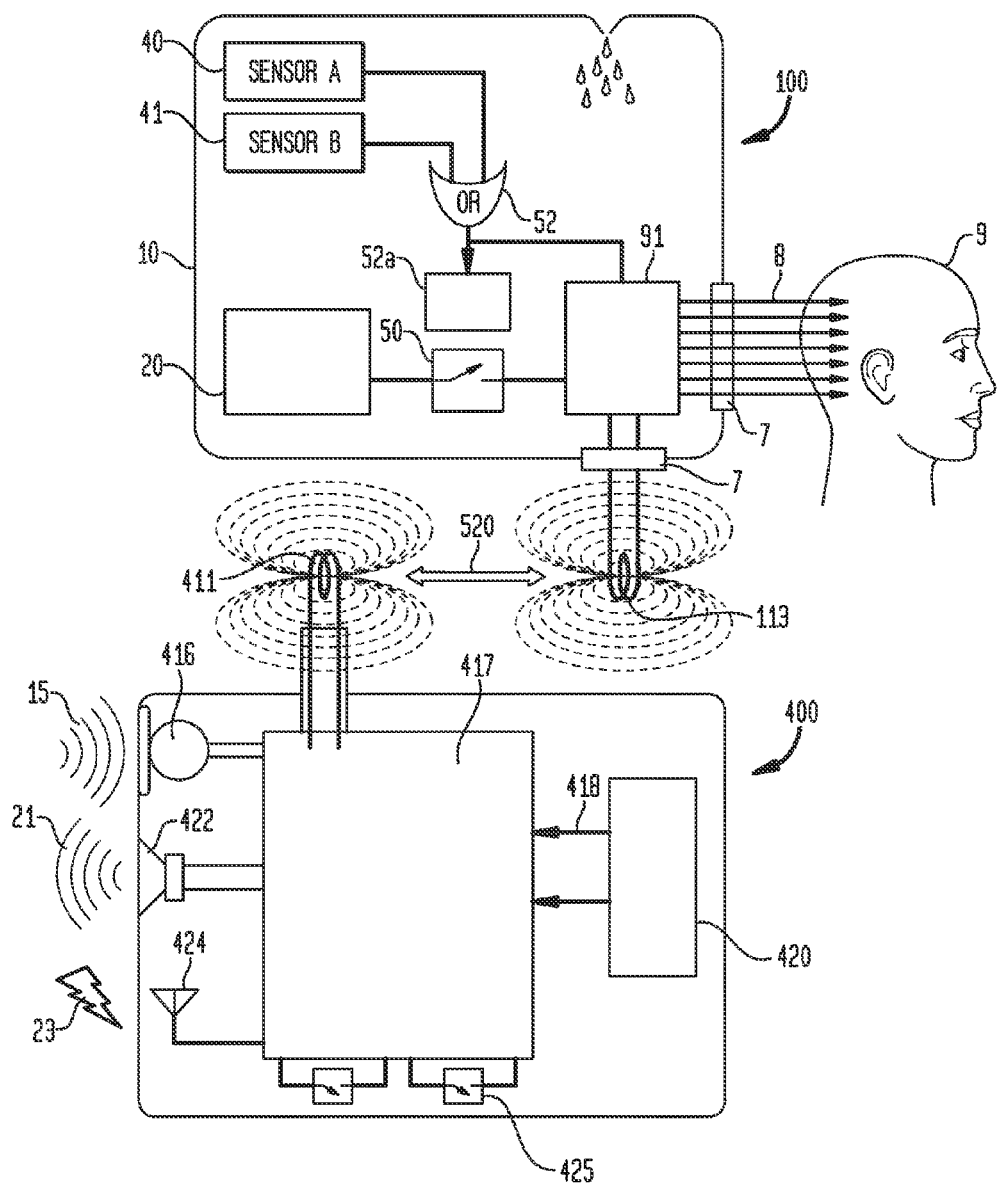
Figure 23:
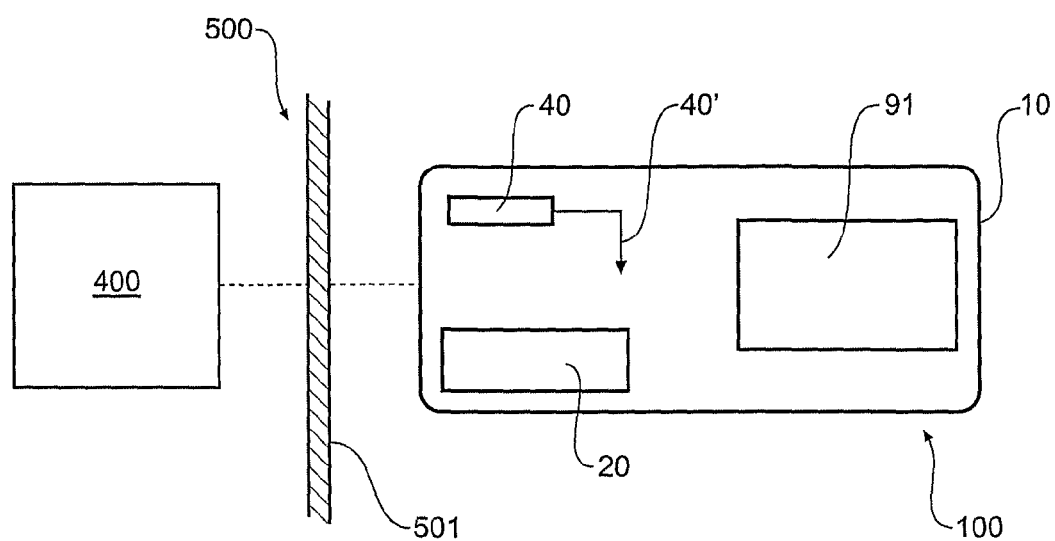

FIG. 4-*shows* a voltage waveform resulting from the disconnect event of FIG. 3;

FIG. 5 is a functional illustration of one arrangement of a medical implant, in accordance with embodiments of the present invention;

FIG. 6 is a functional illustration of another arrangement of a medical implant, in accordance with embodiments of the present invention;

FIG. 7 is a circuit schematic of a power source disconnect switch, in accordance with embodiments of the present invention;

FIG. 8 is a functional diagram of a medical implant incorporating the arrangement of FIG. 6;

FIG. 9 is schematic diagram of an alternative a power source disconnect interface, in accordance with embodiments of the present invention;

FIG. 10A is a schematic diagram of another power source disconnect interface, in accordance with embodiments of the present invention;

FIG. 10B is a schematic diagram of another power source disconnect interface, in accordance with embodiments of the present invention;

FIG. 11 is a schematic diagram further illustrating the power source disconnect interface of FIGS. 10A and 10B;

FIG. 12 is a schematic diagram of a medical implant, in accordance with embodiments of the present invention;

FIG. 13 schematically illustrates the medical implant of FIG. 12 with a rupture in the hermetically sealed casing;

FIG. 14 is a schematic diagram of a power source module, in accordance with embodiments of the present invention;

FIG. 15 is a schematic diagram of one arrangement of a power source module in accordance with embodiments of the present invention;

FIG. 16A illustrates a power source module in a medical implant, in accordance with embodiments of the present invention;

FIG. 16B illustrates the medical implant of FIG. 16A when the medical implant is ruptured;

FIG. 17A illustrates a power source module in a medical implant, in accordance with embodiments of the present invention;

FIG. 17B illustrates the medical implant of FIG. 16A when the medical implant is ruptured;

FIG. 18A illustrates the use of a mechanical transducer to detect a failure in the hermeticity of a medical implant, in accordance with embodiments of the present invention;

FIG. 18B illustrates the medical implant of FIG. 18A, with a rupture in a first half of the implant;

FIG. 18C illustrates the medical implant of FIG. 18A, with a rupture in a second half of the implant;

FIG. 19A is a schematic illustration of one embodiment of the present invention;

FIG. 19B is a schematic illustration of one embodiment of the present invention;

FIG. 19C is a schematic illustration of one embodiment of the present invention;

FIG. 20 is a schematic illustration of an arrangement in which a detection signal is generated to actuate other functions in response to a detected failure in hermeticity, in accordance with embodiments of the present invention;

FIG. 21 is a schematic illustration of a medical implant, in accordance with embodiments of the present invention;

FIG. 22 is a schematic illustration of cochlear implant, in accordance with embodiments of the present invention; and FIG. 23 is a schematic illustration of a medical implant, in accordance with embodiments of the present invention.

DETAILED DESCRIPTION

Aspects of the present invention are generally directed to a medical implant comprising an implantable, hermetically sealed housing. The implant includes a hermeticity failure sensor configured to detect a failure in the hermeticity of the housing, and, following a failure detection, trigger one or more additional operations. In certain embodiments, the implant includes a power source and one or more additional components, and the sensor triggers the disconnection of the power source from the other components. In other embodiments, in response to a failure detection, the sensor triggers the generation of an alarm.

Embodiments of the present invention are primarily described herein with reference to a cochlear implant. However, it will be understood that the various aspects of the present invention may be implemented in other medical implants now known or later developed, such as an Auditory Brainstem Implant (ABI), a Functional Electrical Stimulation (FES) device, a spinal cord stimulator (SCS), etc. An ABI includes one or more electrodes positioned to electrically stimulate acoustic nerves in the brainstem. The stimulating electrical signals are provided by a signal processor processing input sounds from a microphone located externally to the recipient. This allows the recipient to hear a certain degree of sound. FES is a technique that uses electrical currents to activate muscles and/or nerves, restoring function in people with paralysis-related disabilities. Injuries to the spinal cord interfere with electrical signals between the brain and the muscles, which can result in paralysis. SCS systems deliver pulses of electrical energy via an electrode in the spinal area and may be used for pain management.

Figure 1:
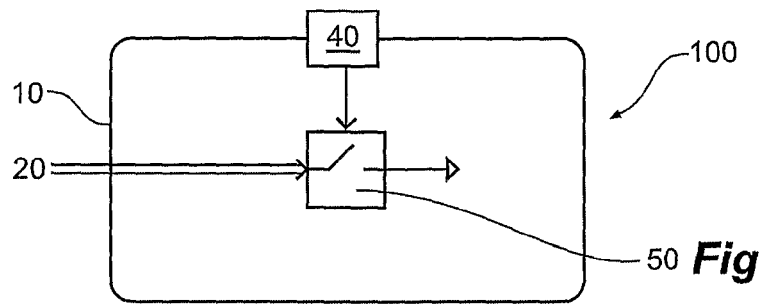
FIG. 1 is a schematic view of a medical implant, in accordance with one embodiment of the present invention.

FIG. 1 is a schematic representation of a cochlear implant 100 of all in accordance with embodiments of the present invention. Cochlear implant 100 includes a hermetic housing or casing 10 and is powered by a power source 20. The power source 20 is illustrated schematically, and it will be appreciated that the power source 20 may be positioned outside the implant 100 (e.g. in a separate power module) or in the implant 100 (e.g. from an internal battery or other internal power source).

Disposed between the power source 20 and any electrically conductive part or element of implant 100 is a disconnect switch 50. When switch 50 is actuated, the switch electrically isolates the power source 20 from the electrically conductive elements. More specifically, implant 100 comprises a disconnect switch interface 40 that, in response to a disconnect event, actuates switch 50 to disconnect power source 20 from the one or more electrically conductive elements. That is, when switch 50 is actuated, power source 20 is electrically isolated from the remainder of implant 100. Thus, there is no part of implant 100 that is electrically live that might then lead to problems if tissue or body fluids of the recipient come into contact with any electrically conductive part of the implant. Interface 40 is shown schematically in FIG. 1 to illustrate that the interface may be disposed either inside or outside of implant 100.

Figure 2A:
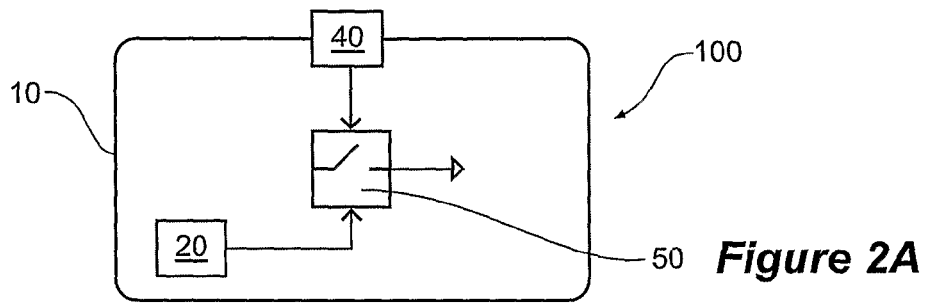
FIG. 2A is a schematic illustration of one arrangement of the medical implant of FIG. 1.
Figure 2B:
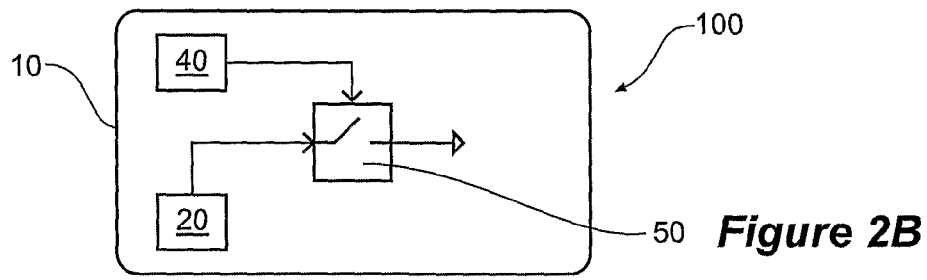
FIG. 2B is a schematic illustration of another arrangement of the medical implant of FIG. 1.
Figure 2C:
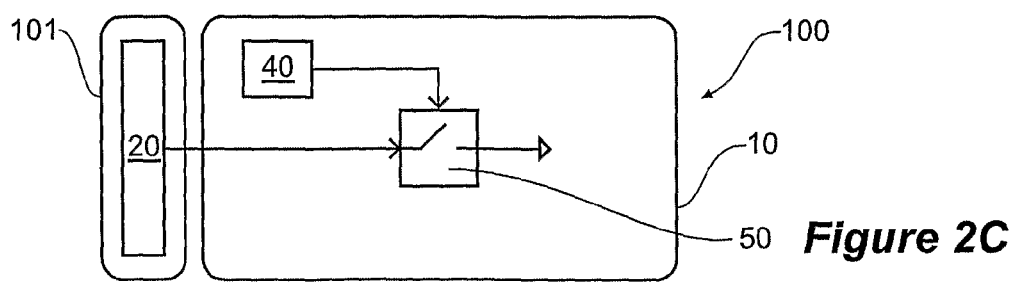
FIG. 2C is a schematic illustration of yet another arrangement of the medical implant of FIG. 1.
Figure 2D:
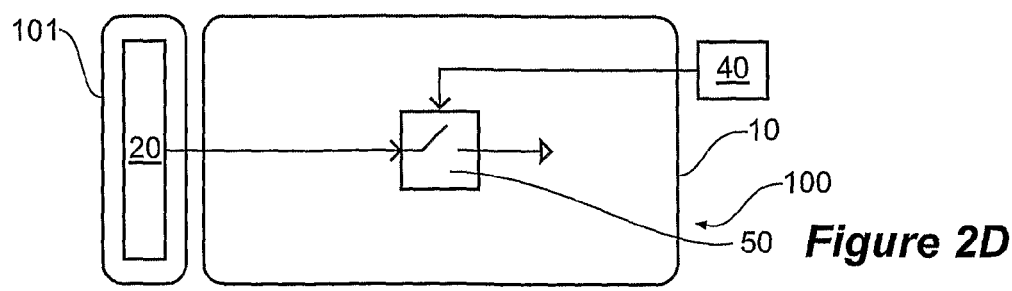
FIG. 2D is a schematic illustration of a further arrangement of the medical implant of FIG. 1.

FIGS. 2A to 2D illustrate various possible combinations of the locations of the power source 20 and disconnect switch interface 40 in relation to implant 100. In FIG. 2A, the power source 20 is disposed inside implant 100 (within housing 10), and the disconnect switch interface 40 is disposed outside implant 100. In FIG. 2B, both the power source 20 and the disconnect switch interface 40 are disposed inside implant 100. In FIG. 2C, the power source 20 is disposed outside implant 100 in a separate power module 101, which may be implanted or located externally of the recipient. In FIG. 2D, both the power source 20 and the disconnect switch interface 40 are located outside the implant 100. It will also be understood that further combinations may be possible, where for example, there are two or more disconnect switch interfaces 40, where one or more might be disposed inside implant 100 and one or more might be disposed outside implant 100.

It will also be appreciated that in some embodiments, the power source module 101, as shown in FIGS. 2C and 2D, may itself be the implant, having the disconnect switch 50 and the power source 20 within the module 101. The module 101 may be used to power another component. Upon detection of an event and subsequent disconnect signal as described further below, the disconnect switch 50 is actuated to electrically isolate the power source 20 from the medical implant being power module 101, as well as the other component that is being powered by power source 20.

In other examples, a medical implant in accordance with embodiments of the present invention may be the combination of a primary medical implant, such as cochlear implant 100 and a power source module 101. Various examples embodying different embodiments will now be described in detail.

According to one aspect of the present invention, a recipient who experiences discomfort due to malfunction or accidental misuse of the device, may temporarily or permanently interrupt the primary power source or supply of electrical or other energy stored within the prosthesis. As such, any discomfort attributable to the power source is alleviated.

As noted above, a disconnect switch interface in accordance with embodiments of the present invention actuates a switch to disconnect a power source from the one or more electrically conductive elements in response to a disconnect event. In certain embodiments, the interface and switch are part of an emergency power disconnection system for use in a totally implantable hearing prosthesis. In certain such embodiments, the disconnect event is receipt, by the interface, of an audio signal having a particular amplitude, frequency, or spectral component. In such embodiments, the audio signal is detected by the sound-receiving microphone of the prosthesis, and interface determines that the audio signal has the specific characteristic triggering disconnection of the implanted battery or power source. In one example, the disconnect event is three knocks of a finger knuckle joint upon a recipient's skull, as represented in FIG. 3. These three knocks are converted to electrical signals by a microphone, and then processed electronically, in any combination of analog and or digital form, so as to trigger a break to the electrical connection between the battery and the electronics circuitry of an implanted prosthesis. In this example, the microphone and processing electronics act as the disconnect switch interface 40 to generate the disconnect signal to actuate the disconnect switch 50 as shown in FIG. 1 for example.

Inadvertent operation of this emergency switch in response to normal incoming sounds is largely prevented through the use of frequency selective, band pass filters that reject all but the spectral components of head knocking Electronic temporal discrimination is also applied to distinguish the repetitive transient characteristic of head knocking as well as to count the number of knocks. Activation of the emergency off switch, thus only occurs when just three knocks are detected within an acceptable time period spanning for example, 1 to 4 seconds. The relatively high loudness of the knocking sound, compared to most other sounds further adds to the unlikelihood of inadvertent operation since the threshold level of sound required for activation can be set to levels seldom achieved by normal everyday sounds.

The low duty cycle transient nature of such head knocking signals is demonstrated in FIG. 4 which shows a plot of output voltage versus time from an actual microphone implanted within the head of a person while their head was tapped as described. The signal displayed by this example is typical of the signal that would trigger the emergency off switch (or disconnect switch) to operate.

In an alternative arrangement, the disconnect event could be detection of a single tap, or two taps, to the skull, as is described in US Patent Application No. 2003/0171787 (previously incorporated by reference) which describes various means of providing a shut down function to parts of a control circuit. In accordance with one aspect of the present invention, the signal generated from this described arrangement could be used as a disconnect signal to cause the energy storage device or battery to disconnect from the remainder of the circuit.

In one embodiment, component 100 is an implantable cochlear implant. FIG. 5 illustrates the main functional blocks of cochlear implant 100 according to this aspect of the present invention. As shown in FIG. 5, cochlear implant 100 comprises a microphone 110 that converts received audio signals to electrical signal. The electrical signal is provided to signal conditioner and filter 120 for discriminating specific audio signals having particular spectral and temporal characteristics (such as tapping). Signal conditioner and filter 120 then provides a signal to signal event detector and counter 130 for detecting and counting events meeting the specified criteria to be classified as a tap. Upon determining that the input sound results from three taps to the recipient's skull, a disconnect signal is generated by signal event detector and counter 130 and provided to disconnect switch 50, which then disconnects energy or power source or battery 20 from the rest of the implant 100. In one embodiment, the battery 20 and disconnect switch 50 may be encased in a high strength and hermetically sealed container 101. While in this embodiment, disconnect switch 50 is disposed inside battery casing 101 with the battery or power source 20, it will be appreciated that in other embodiments, disconnect switch 50 may be disposed outside the battery casing 101 and cochlear implant 100 itself. In other embodiments, there may be no additional casing around battery or power source 20. Battery charging and power distribution functions may be provided by block 140.

In these embodiments of the preset invention, implanted cell, battery of cells or energy or power source 20 are disconnected and isolated from the remainder of implant 100 when the head is tapped three times. In this configuration, re-connection of the battery may be possible by the recipient. For example, in one embodiment, connection may be re-established by the recipient tapping their knuckle ten times (for example) on the side of their head over a period of, for example, 4 to 12 seconds. In this arrangement, the same signal processing will be conducted, generating a "connect signal" to re-connect battery 20 to the rest of the circuit.

In an alternative arrangement, re-connection may be accomplished through a wireless link 160 that uses RF or IR signals, as shown in FIG. 6. FIG. 6 further illustrates a resistor network 102, comprising high value resistors, that limits available battery current to a low and safe value, even in the event of a single component failure, yet sufficient to preserve the functionality of the sound-initiated disconnect system.

FIG. 7 shows a more detailed arrangement of the disconnect switch 50 within casing 150, connected to battery 20. In this embodiment, the principals of multiple redundancy is used to achieve partial immunity to component failure, thereby providing substantially high reliability in disconnecting the battery supply of an implanted hearing prosthesis. In this regard, multiple banks of parallel resistors 7, 8, 9, 18, 11, 13 and 14 are used.

In this circuit, the normal supply of battery power through the two series connected, field effect transistors (FETs) 1 and 2 results from their "switched on" low resistance state. This is caused by the application of a voltage to their gate terminal that is more negative than their source terminal. This gate to source voltage, supplied from the latching circuits, falls to almost zero when an appropriate negative going voltage, as initiated when battery disconnection is desired (via switch 12 provided in one embodiment, by signal event detector and counter 130 from FIGS. 5 and 6), is conveyed to the input of both latch circuits 3 and 4. With almost zero, gate to source voltage, the internal source to drain resistance of both FETs 1 and 2 increases significantly to such an extent that the supply of battery current to other prosthesis circuitry beyond the barrier 150 (indicated by the dashed line) is virtually zero. Power source de-coupling capacitors 15 and 16 are also shown in FIG. 7.

FIG. 8 illustrates the main functional blocks of a cochlear implant 100 incorporating one aspect of the invention. As shown, implant 100 includes a microphone 110 for receiving sound (such as the sound of tapping on the recipient's skull). The converted sound signal is then applied to analog to digital converter (A/D) 160 to convert the analog electrical sound signal from microphone 110 (as conditioned by signal conditioner 120) into a digital signal. The digital signal is input to neural stimulation and current delivery control circuits 170 to generate stimulating signals corresponding to the digital signal. The stimulating signals are input to electrode switching circuitry 180 which processes and applies the stimulating signals to cochlear electrode array 230 for stimulation of the recipient's cochlea.

The remaining blocks 190, 200, 210, 220 and 140 are part of a conventional cochlear implant as will be understood by the person skilled in the art.

As previously described, in accordance with this aspect of the present invention, signal conditioner 120, also applies a signal to signal event detector and counter 130, which, upon determination of the surrounding sound as three taps to the skull in this example, generates a disconnect signal to battery or power source disconnect switch 50. This will then disconnect battery 20 from the remainder of the implant 100 as previously described.

It will be understood that any other suitable recipient interfaces or means of generating a disconnect signal may be used in this aspect of the invention. For example, in US Patent Application No. 2003/0171787 (previously incorporated by reference), a control signal is generated to control various parts of the implant by various means. According to this aspect of the invention, this control signal could be used an event to generate the disconnect signal to disconnect the battery 20 from the remainder of the implant. In this US application, in one example, the control signal is generated upon the detection of a single, or two taps to the recipient's skull. In another example, the recipient interface is by way of a magnetic switch in the implant circuitry which may be activated by an external magnet, or an implanted magnet. In other examples, the recipient interface could be a compliant membrane switch or a piezo electric switch, each as described in the incorporated US patent application.

U.S. Pat. No. 6,358,281 (previously incorporated) describes a number of other arrangements that could be used as a recipient interface for this aspect of the present invention. In particular, described therein is a pressure switch that can be actuated by the recipient (another example of an event), a magnetic switch that can be actuated by the recipient by way of an external magnet, and an external data transmitter that is able to generate instructions via various wireless links including radio frequency (RF) and infra red (IR).

In International Patent Application No. PCT/AU96/00403 (WO97/01314), (previously incorporated by reference), there is described a method of generating control signals within a cochlear implant using specific audio instructions, including voice commands from the recipient. Such an arrangement may also be used as the disconnect switch interface to generate the disconnect signal in response to the event of the audio instructions, for use in this aspect of the present invention.

Various other alternatives to the examples are described above are possible using a variety of manually-activated controls, switches and transducers to detect human intervention as examples of an event, intended to initiate the disconnection of energy or power sources such as batteries.

In the example shown in FIG. 9, disconnect switch 50 is provided by a magnetically-actuated electrical switch, (in one example, a magnetically latching reed switch 51), which is used as a bi-stable element to break or interrupt the supply of battery power to the rest of the electronic circuitry of implant 100. Alternatively a non-latching reed switch can be used to either interrupt or establish an electric current so as to trigger an electronic bi-stable circuit element such as a flip-flop into changing state so as to cause the conductivity of the electronic switching component to which it is connected to interrupt or disconnect the battery or energy source. Such a switching component may be a field effect transistor (FET), since the total electrical energy required to maintain this current controlling component in a state of electrical conduction or insulation is small and thus has little impact on the period over which a battery powered prosthesis can operate per discharge cycle.

As shown in FIG. 9, the proximity of a permanent magnet 49 applies a sufficiently strong magnetic field to the reed like contacts of the reed switch 51 so as to hold them together and in electrical contact. When an implanted recipient wishes to disconnect their battery, they have the option of momentarily pressing a finger 42 against their head at a position between the implant 100 and its associated magnet 49. This event causes the magnet 49 to move away from the implant 100, weakening the magnetic force applied to the reed switch 51 until its contacts open momentarily. This momentarily interrupts the supply of electric current to a flip-flop circuit, causing it and the switching device to which it is connected to interrupt the supply of battery energy to the implant circuitry.

By depressing the skin again, the recipient can trigger the flip-flop circuit into changing state so that the supply of battery energy is restored. Thus in this embodiment, disconnect switch interface 40 is provided by the combination of magnet 49 and finger 42.

Yet a further disconnect switch interface will now be described with reference to FIGS. 10A and 10B of FIG. 10. In addition to allowing the battery or energy or power source of an implanted prosthesis to be disconnected at the discretion of the recipient, certain embodiments of the present invention are directed to automatically causing disconnection of a power source from other components of the implant. For example, this automatic disconnection may occur when the medical implant is subjected to an event such as an impact or when acceleration forces are applied either manually by a recipient, or due to an accident or misadventure likely to damage the implant 100.

Embodiments of the present invention are configured such that normal, everyday impacts to a recipient's head or implant site have little or effect on the operation of a medical implant. However, a high impact event such as collision with a ball (cricket, golf or baseball), or other serious impact such as in a bike or vehicle accident, functions as a disconnect event that triggers automatic disconnection of the battery or energy or power source to other elements of the medical implant 100.

In one example, use is made of an inertial mass, which when acted upon by the acceleration forces that accompany an impact, applies a physical force that breaks or severs the electrical contact with the battery or energy supply circuit. This forms an acceleration-activated switch. In this arrangement, both the disconnect switch interface and the disconnect switch are provided by the acceleration-activated switch. In further embodiments, a magnetically operated switch (such as a reed switch), can be optionally included as a means to temporarily bypass an already actuated emergency cut-out switch for diagnostic or other purposes.

In FIG. 10A, there is shown switch 30 acting as the disconnect switch interface and disconnect switch. Switch 30 has electrical terminals 31 and 32, and a spring 33 supporting an electrically conductive mass 34. In this embodiment, surrounding terminal 32, is a mass receiving element 35 having a portion 36 for receiving mass 34. Surrounding portion 36 is a second portion 37, which when mass 34 is received therein, prevents mass 34 from electrical contact with terminal 32, thus shutting off the switch. These elements are all housed within an electrically non-conductive housing 38.

In the embodiments of FIGS. 10A and 10B, prior to activation, an electrical circuit is established between terminals 31 and 32 via electrically conductive helical compression spring 33 and ball/mass 34. The ball, which is confined within a shallow, electrically non-conductive recess, establishes the circuit by its direct contact with the conductor or terminal 32. When the switch housing is acted upon by sufficient lateral force (represented by the arrow as seen in FIG. 10B), the housing 38 moves relative to the ball or mass 34. This has the effect of relocating the ball 34 in electrically non-conductive recess or portion 37. This not only severs the electrical contact between the ball and the terminal 34, but the depth of the recess 37 captures and retains the ball 34. The force applied by the compression spring 33 provides further retaining force to ball 34 to keep it in recess 37, and thus keep the switch open/off.

In one embodiment, mass receiving element 35 would be shaped to have a circular portion 36 for receiving the ball 34 for electrical contact, and be surrounded by a circular portion forming non-conducting portion 37, in effect, forming two concentric "channels".

FIG. 11 shows one possible embodiment using the acceleration switch of FIGS. 10A and 10B. In this embodiment, there is shown cochlear implant 100 with disconnect switch interface 40 connected to battery 20 that supplies power to the remainder 90 of the cochlear implant 100. In this embodiment, three acceleration switches 30, 30' and 30" that are similar to the switches of FIG. 10 are placed in series in the supply path of battery 20. These can be disposed orthogonally to the direction of expected impact force, or at least partially aligned in such a manner as to be most sensitive to potentially damaging acceleration and intentional activation forces. Once the emergency cut-off switch has been activated, an optional glass encapsulated magnetically actuated reed switch 60, allows the circuitry to be reactivated using a permanent magnet 70 from outside the body for diagnostic or temporary emergency re-activation purposes.

It will be understood that any number of acceleration switches 30 could be used, including 1, 2, 3, 4, 5 or more. The use of more than one in series provides higher switch-off reliability.

According to another aspect of the present invention, disconnect switch 50 may be actuated upon the event of the hermetic casing of the medical implant 100 being ruptured or otherwise compromised, thereby leading to the risk of biofluids entering the implant 100 and coming into contact with electrical elements. In one such embodiment, the disconnect switch interface 40 may be provided by a hermeticity sensor 40.

More specifically, in embodiments of the present invention, a medical implant comprises an implantable, hermetically sealed housing, and a hermeticity failure sensor configured to detect a failure in the hermeticity of the housing. Following a failure detection, the sensor triggers one or more additional operations.

FIG. 12 shows a simplified schematic of a medical implant 100, in this case, a stimulator 100 of a cochlear implant system, that includes a hermeticity failure sensor. Stimulator 100 comprises a hermetically sealed container 10, which houses functional electronics 91 for processing data and generating stimulation signals for stimulating nerve fibers in a recipient's cochlea by way of an electrode array (not shown). The hermetically sealed container 10 also houses a power source 20 for providing power to the functional electronics 91.

As previously described, if hermetically sealed container 10 ruptures (a further example of an event) while it is implanted within the recipient, surrounding biofluids will leak into the stimulator and come into electrical contact with electrical power through, for example, the functional electronics 91 or directly with the power source 20. When the biofluids enter the container, they fluids will bridge electrically powered circuitry. As such, the ion rich, aqueous body fluids would be subject to electric current flow, electrolysis and subsequent production of toxic substances. Under the pressure created by the electrolytic evolution of gaseous components, these toxic substances might be expelled into surrounding body tissue with dire effect to the user or recipient. Furthermore, the recipient may be further put at risk if there is provided a new and undesirable current path to other parts of the recipient's body, through biofluids now contacting electrical current.

Thus, according to one aspect of the present invention, and as shown in FIG. 12, implant 100 may include a hermeticity failure sensor. In the embodiments of FIG. 12, the hermeticity failure sensor is a pressure sensor 40, which is connected to a disconnect switch 50, disposed between power source 20 and the rest of the implant 100.

In the case of traumatic event such as a significant impact to the recipient's head, hermetically sealed casing 10 may become ruptured as shown in FIG. 13. This allows for the ingress of biofluids 600 into the casing or container 10, to allow contact with functional electronics 91 and/or power source 20.

In accordance with this aspect of the present invention, pressure sensor 40, acting as the disconnect switch interface, will detect a change in pressure and generate and send a disconnect signal to disconnect switch 50. The disconnect signal actuates switch 50 so as to electrically isolate the power source from the other electrical components. As such, any electrical power to the implant 100 is ceased so as to prevent any consequential damage. This will also act as a trigger to the recipient that there is a problem with his implant, and seek professional assistance.

The pressure change within the hermetically sealed container may be a sudden reduction in pressure as internal gases escape from the container 10. In other embodiments, the pressure change is more likely a pressure increase within the container 10 as the biofluids seep into the container 10 through the rupture and begin generating gases upon contact with electrical power.

In one form, the power source disconnect switch may be provided by an arrangement as above with reference to FIG. 7.

In one example, the pressure sensor 40 may be provided by a piezo resistive strain gauge. Combined with suitable electronics, such a system could provide a reliable pressure detection threshold of, for example, 50 millibars for a fully implanted hearing prosthesis with an internal air or gas volume of about 1 cubic centimeter or 1 milliliter, yielding a leak detection threshold of about 50 micro liters.

In another form of the present invention, the pressure sensor 40 and disconnect switch 50 may be provided by, or as part of, a power source module 300 as shown in FIG. 14. Power source module 300 has a power source module hermetically sealed container or casing 310, a first contact 320 connected to a power source 340 such as a battery, and a second contact 330 for connection to a power sink or drain such as the functional electronics 91 previously described. As can be seen, pressure sensor 40 may be provided as a part of power source module 300, to act on the first and/or second contacts 320,330 to disconnect the power source 340 from the rest of the implant. As previously described with reference to FIGS. 2C and 2D, power source module 300 in this arrangement, may be the medical implant 100 itself.

In one form, the pressure sensor 40 of the power source module 300 may be provided by a flexible or moveable portion 41, which, upon a differential pressure between inside and outside hermetically sealed casing 310 (another example of an event), will flex one way or another (outwardly if the internal pressure is greater than the external pressure and inwardly if the internal pressure is less than the external pressure). FIG. 15 shows this arrangement with power source module 300 having hermetically sealed container 310, power source 340, pressure sensor 40 being provided by flexible portion 41 (in one example, a flexible membrane), and first and second electrical contacts 320 and 330. Also shown are corrugations 42, surrounding, or partially surrounding flexible portion 41. These may be optionally provided to enhance the action of the flexible portion. Flexible portion 41 and/or corrugations may for example, be provided by a flexible membrane made from 0.1 mm thick, sheet of biocompatible material such as surgical grade stainless steel or titanium metal, or may be provided by a flexible portion of the same material as the hermetically sealed casing which has been appropriately shaped, heat-treated or weakened, or a combination of both or other materials.

Also provided is a displacement or coupling member 350 which is disposed between flexible portion 41 and one of either first or second contacts 320, 330. The coupling member may, for example, be provided by an electrically non-conducting material such as a vitreous glass or ceramic or a polymer such as polyurethane, polyethylene or silicone elastomer.

The operation of power source module 300 will now be described with reference to HG. 16A. FIG. 16A shows power source module 300 located inside a hermetically sealed container 10 of a medical implant 100, such as a stimulator of a cochlear implant. For clarity, the functional electronics 91 shown in FIGS. 12 and 13 have been omitted.

In FIG. 16A, it can be seen that contacts 320 and 330 are in contact with one another, and power source module is therefore able to provide power to the rest of the device. It will be appreciated that while the contacts 320 and 330 are shown "floating in space" and not connected to anything, that this is a schematic representation and that in practice, one of contact 320 or 330 will be connected to power source 340 and the other of the contacts will be connected to the rest of the circuit, including functional electronics 91.

During manufacture, the internal pressure of the power source module 300 has been made to be greater than the internal pressure within the hermetically sealed container 10 of the stimulator or medical implant 100. As such, flexible portion 41 is bowed outwards. The relative pressures may be controlled by controlling the pressure within the power source module or within the stimulator, or a combination of both. In one example, the internal pressure of the stimulator may be controlled to be about 0.5 Bar less than the internal pressure of the power source module, by setting of an air or gas pressure within the hermetically sealed casing of the stimulator. This is generally set to be about equal to the pressures of what would be expected in vivo.

In FIG. 16B, there is shown the arrangement of FIG. 16A in which hermetically sealed container 10 of the stimulator 100 has been ruptured, allowing the ingress of biofluids 600. As previously described, this will result in an increase in internal pressure of the hermetically sealed container 10, thus increasing the external pressure on the power source module 300. This in turn causes flexible portion 41 to push inwards, also pushing down coupling member 350. This in turn pushes on second contact 330, pivoting this away from first contact 320, opening the circuit and effectively disconnecting or isolating power source 340. Accordingly, any biofluids within hermetically sealed container 10 will no longer be exposed to electrical power, reducing the propensity for consequential injury to the recipient. The subsequent interruption of electrical power and cessation of implant functionality are also of benefit in raising the malfunction to the attention of a recipient, who might otherwise remain unaware of a potentially hazardous, partial malfunction.

This arrangement of medical implant 100 with power source module 300 may be used in a medical implant system 500 comprising an external component and the medical implant. For example, in the case where the medical implant system 500 is a cochlear implant system, the external component 400 is a sound processor and the internal, medical implant 100 is a cochlear implant.

FIG. 17A shows an alternative arrangement of power source module 300 within hermetically sealed container 10. In this arrangement, flexible portion 41 is provided in a different region such that an increase in pressure in the hermetically sealed container 10 (due to a rupture for example, as shown in FIG. 17B) will result in the displacement of coupling member 350 upwards instead of downwards as previously described. In this arrangement, coupling member 350 is operationally connected to first contact 320 such it pulls first contact 320 away from second contact 330 to open the circuit, as shown in FIG. 17B.

FIGS. 18A, 18B and 18C represent a cross sectional view of yet another alternative configuration whereby the interior volume of an implant 100 housing or casing 10, is pressurized to below ambient pressure within the body and is separated into two, approximately equal sized, gas tight sections 704 and 706, by a flexible dividing member 701. In these views, for ease of illustration, the functional electronics, the power source and the power source disconnect switch are not shown.

One or more electrical conductors, cast into a block of electrically non-conductive material, form a hermetic electrical feed through member 705. This member allows electrical circuit currents to pass between sections, while at the same time preserving a hermetic gas tight separation of both sections.

A mechanical transducer, in this case, piezo-resistive strain transducer 702 is attached or coupled to the surface of the flexible dividing member 701 such that a proportion of any mechanical strain applied to the flexible dividing member 701, will also be conveyed to the transducer 702. Electrical circuitry, (which has not been shown to aid clarity), constantly or periodically senses the electrical resistance of this transducer, and hence the strain force applied to the dividing member.

Under conditions of normal use, as illustrated by FIG. 18A, this strain force is relatively small since the pressure of the gas filling both sections of the implant housing is largely equal, as represented by the more or less flat surface of the dividing member 701.

In FIG. 18B, a rupture or breach 650 of the implant housing, is shown to have caused ingress of body fluid 600 and, a relative increase to the internal pressure within section 706 of the implant housing. The resultant pressure difference between sections 704 and 706, applies mechanical force to the dividing member 701 and a tensile force to the strain transducer, as suggested by the surface curvature of the dividing member 701.

On detecting the subsequent increase to the electrical resistance of the transducer, the electrical circuitry is configured to generate a signal to alert the implant recipient and isolate or disconnect the stored energy source.

A rupture 650 affecting the other section 704 of the implant housing, as shown in FIG. 18C, creates a similar effect in that it too produces a pressure difference between sections. However, this pressure difference is in the reverse direction as illustrated by the reverse curvature of the dividing member 701. In this case, the resulting strain applied to the transducer is compressive, and thus causes an equally detectable reduction to the electrical resistance of the strain transducer.

As those skilled in the art will appreciate, numerous other alternatives to the pressurization scheme and configuration illustrated in FIGS. 18A, 18B and 18C can be applied to detect and ameliorate the implant hermeticity failures.

It will also be appreciated that, in certain circumstances, a rupture in the hermetically sealed container of the implant might lead to a decrease in internal pressure. In such circumstances, the internal pressure of the power source module may be manufactured to be less than the expected internal pressure of the hermetically sealed container of the implant. More specifically, in this case, the arrangement of flexible dividing member 701 and/or other equivalent elements and coupling member 350 would be adjusted or rearranged accordingly, such that a change in pressure will result in a disconnection of the power source.

It will also be understood that the flexible portion may be directly connected to one of the switch contacts, without a coupling member being disposed therebetween.

It will also be appreciated that the hermeticity failure sensor 40 need not be limited to a pressure sensing arrangement as provided in one form by the arrangement of FIGS. 16-18. A rupture in the hermetic container may be detected by sensing other parameters such as for example, the increase or reduction of a fluid or liquid in the container, an increase in light within the container, and increase in sound within the container. Accordingly, the hermeticity failure sensor 40 may be provided by any other suitable sensing arrangement to infer a hermeticity failure by other means such as, but not limited to; accelerometers to detect excess mechanical shock, humidity or surface moisture transducers that detect fluid ingress, gas sensors that detect loss of a specific gas incorporated within the hermetic protective member implant, transmitting and receiving acoustic transducers that detect internal volumetric changes due to fluid ingress, and one or more light sensitive photo PIN diodes that detect traces of ambient light leakage through any puncture or breach in an otherwise, normally opaque hermetic implant housing.

In some embodiments, more than one sensor may be used to detect failure of the hermetically sealed container. In FIG. 19A, there is shown the implant 100 with hermetically sealed container 10, battery 20, functional electronics 91 and disconnect switch 50. In this arrangement, two sensors or transducers 40, 41 are used to detect hermeticity failure. For example, sensor A (40) and sensor B (41) could both be moisture sensors, located at different places within the implant 100, to increase the likelihood of detection of fluid ingress. Alternatively, one or more moisture sensors could be used in combination with one or more gas sensors or gas pressure sensors.

Logic circuits 51, 52 may be used to control the result of the output of the various sensors used, as shown in FIGS. 19A, 19B and 19C. While the examples of FIGS. 19A, 19B and 19C use digital logic gates to combine or process transducer status signals to improve hermeticity failure sensitivity and reliability, those skilled in the art will appreciate that other forms of digital or analog signal processing can be used with any combination or number of transducers or sensors, to similar effect.

The example shown in FIG. 19A uses a digital logic AND gate circuit (52) to interrupt the supply of stored energy only when both two sensing transducers detect a failure in hermeticity. This combination might for example be used to reduce the probability of falsely detecting a hermeticity failure due to failure of one sensor or transducer.

The example shown in FIG. 19B uses a digital logic OR gate circuit (51) to interrupt the supply of stored energy when either transducer detects a failure in hermeticity. In this example, the supply of stored energy would still be interrupted after a failure of hermeticity, despite a failure of either transducer.

The example shown in FIG. 19C uses a combination of AND (52) and OR (51) gates to interrupt the supply of stored energy when sensor A (40) AND B (41) both detect a failure in hermeticity OR when sensor C (42) detects a failure in hermeticity.

It will be appreciated that any other combination and number of sensors, transducers and logic circuits or functions could be used to detect hermeticity failure and may be tailored for a particular application. It will also be appreciated that the logic functions may be provided by any means such as an integrated circuit or as a programmed function of a microprocessor.

In a further variation, there may be situations where the implant continues stimulation for a short period during, which an easily recognizable alarm is conveyed to the recipient, before power is shut off. As one skilled in the art will appreciate, this alarm could take the form of neural stimulation representing or perceived as; a unique acoustic sound or series of tones or spoken language instructions.

It will also be appreciated that the arrangements described above may be used as hermeticity failure detectors 40, in their own right, with the detection signal being used for other functions not necessarily relating to power source disconnection. For example, the detection may be used simply to issue an alert or alarm. In other examples, the detection signal may be used to disconnect an external power source, for example provided by a battery in an externally-placed processor, providing power subcutaneously for example. In this case, a disconnect switch for the external power source may be provided in the external processor or in a pathway in the internal stimulator.

In other examples, the detection signal need not be used to disconnect a power source, but may rather be used simply to issue an alarm warning of a hermetic failure, may be used to shut off other parts of the circuitry, or may initiate any other function that may be deemed desirable in the event of a detected failure in hermeticity.

It will be understood that in another aspects of the present invention, some embodiments need not have the power source disconnect switch 50. In these embodiments, when the hermeticity failure sensor (whether this is comprises a single sensor or a plurality of sensors) detects a rupture in hermetic casing 10, the result is a detection signal which may be used to actuate other functions, other than to actuate the disconnect switch 50.

FIG. 20 shows the arrangement of FIG. 19A without a battery disconnect switch. In this example, the output of the one or more sensors provides the detection signal (in this example the output is shown as the output of the AND gate, however, in an application with a single sensor, the output may come directly from the sensor itself). This detection signal may then be applied to actuate an alarm or any other desired function in response to the detected failure in hermeticity. For example, the actuated action may be to cause a display external to the recipient to indicate the detection of a rupture in the medical implant, or in another example, to issue a set audio signal to the recipient, perhaps generating the words "Rupture detected". In other embodiments, the detection signal may be used to generate a message for transmission to a remote monitoring station in the recipient's home or in the premises of the recipient's healthcare provider.

FIG. 21 shows a general arrangement of a medical implant system 500 to which the various aspects of the present invention may be applied. In FIG. 21 there is shown the medical implant system 500 with external component 400 and internal implant 100. Implant 100 as previously described includes functional electronics 91, power source disconnect switch 50, hermeticity failure sensor 40 and power source or battery 20.

External component 400 may provide recipient-interface or other processing functionality. External component 400 may communicate with the internal implant 100 through tissue barrier 501 via any suitable method including a physical, hard-wired connection, or wireless system, such as an inductive or IR link.

As previously described, if hermeticity failure sensor 40 detects a failure in hermeticity, it may generate a signal as a trigger for performing certain functions. Functions include, for example, actuating power source disconnect switch 50 to disconnect power source or battery 20 from the rest of the implant, and/or for issuing an alert or performing some other function.

FIG. 22 illustrates a cochlear implant system 500, in accordance with one embodiment of the present invention. As shown, system 500 comprises an external component 400 being a sound processor, and an internal implant 100 being a stimulator. Implant 100 is, in use, implanted within the implantee or recipient 9.

Chemical energy stored within a cell or battery of cells 420 supplies electrical energy via the wiring 418, to an electrical circuit 417. When incoming sound 15, impinges upon microphone 416, an electrical audio signal is produced and conveyed to the electrical circuit 417.

Under discretionary control of the recipient, as captured by the recipient interface switches 425, this circuit uses various parameters and stored program instructions to extract audio information from the microphone signal. The extracted audio data is encoded for transmission and conveyed to an electromagnetic induction coil 411 via a short length of cable 414.

A significant proportion of the energy 520 radiated by the induction coil 411, is received by a second induction coil 113, associated with the implanted component 100. The received signal is conveyed to the functional circuitry or electronics 91 where the bulk of the electrical energy is extracted to power the implanted part and or to charge its battery 20 via the battery disconnect safety switch 50.

The extracted data component is decoded and processed to control the implanted part and the characteristics of the electrical currents that are delivered to the electrodes 8 that stimulate the neural centers of recipient 9. As with the wiring of the induction coil, the wiring that connects the implant functional electronics 91 to the stimulating electrodes 8 pass through hermetically sealed electrical feed through insulators 7.

The outputs of two hermeticity failure detection sensors or transducers 40 and 41, are functionally combined by a logical gate circuit 52 (in this case an "OR" gate). The output of the logical gate circuit 52 triggers the implanted circuit or functional electronics 91 to convey a warning of hermeticity failure to the recipient 9, either directly via an alarm consisting of a unique pattern of applied neural stimulation current, or by firstly conveying data indicative of the hermeticity failure to the external control circuit 417 via the two inductions coils 113 and 411.

On receipt of this hermeticity status alert, the external circuit 417 in this example causes an acoustic alarm signal 21 to be emitted from a tiny speaker 422. The external circuit 417 may also produce a wireless transmission signal to be conveyed to a radiating antenna 424.

The electromagnetic energy 23, thus radiated and encoded with information of the hermeticity failure can be received by a nearby wireless device, such as Bluetooth™ like device, that will also sound an alarm or flash a light to alert the recipient, healthcare provider, guardian of a young infant recipient, etc., of the failure. For an adult recipient, circuit 417 can be optionally programmed to convey neural stimulation data back to the implanted part, which thereby invokes a neural response perceivable as a spoken message informing the recipient of the hermeticity failure.

The hermeticity failure detection signal output of the "OR" gate 52, may also pass to a time delay circuit 52A, which after the prescribed time delay designed or programmed into the delay circuit has elapsed, causes the battery isolation or disconnect switch 50 to sever the electrical circuit of the battery supply. The 30-second (for example) nominal time delay provided by 52A, allows the implant system to remain powered and functional whilst the various hermeticity failure alerts and alarms are processed and delivered as described.

FIG. 23 shows a medical implant system 500 with medical implant 100 and external component 400, communicating through tissue 501 of a recipient. In the case of a cochlear implant system 500, the medical implant 100 is a cochlear implant and the external component is a sound processor, for example, as described above with reference to FIG. 22.

In the arrangement in FIG. 23, the medical implant system uses an embodiment similar to that described with reference to FIG. 20, in which there is no power source disconnect switch. In this embodiment, upon hermeticity failure sensor 40 detecting a rupture in hermetic casing 10, a detection signal 40' is generated, which may then be used to actuate any other system as described above. In one form, of course, the detection signal may act as the disconnect signal in the embodiment of FIG. 22.

The reference to any prior art in this specification is not, and should not be taken as, an acknowledgement of any form of suggestion that such prior art forms part of the common general knowledge.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

The invention claimed is:

1. A medical implant, comprising:
a hermetically sealed housing; and
a hermeticity failure sensor configured to:
   detect a failure in hermeticity of the housing based on a change in sound and at least one of a change in brightness, pressure, volume, atmospheric composition in the housing and acceleration to which the medical implant is subjected; and following a failure detection, trigger one or more additional operations.

2. The medical implant of claim 1, wherein the hermeticity failure sensor comprises a pressure sensor.

3. The medical implant of claim 1, wherein the hermeticity failure sensor comprises a humidity sensor.

4. The medical implant of claim 1, wherein the hermeticity failure sensor comprises a surface moisture sensor.

5. The medical implant of claim 1, wherein the hermeticity failure sensor comprises an accelerometer configured to detect shock applied to the housing.

6. The medical implant of claim 1, wherein the hermeticity failure sensor comprises a gas sensor configured to detect egress of a gas contained within the housing.

7. The medical implant of claim 1, wherein the hermeticity failure sensor is further configured to detect volumetric changes in the housing resulting from ingress of fluid.

8. The medical implant of claim 1, wherein the hermeticity failure sensor comprises a light sensor configured to detect a change in brightness in the housing.

9. The medical implant of claim 1, comprising a power source electrically connected one or more other electrical components,
wherein the one or more additional operations comprise an electrical disconnection of the power source from the one or more other electrical components.

10. The medical implant of claim 1, wherein the one or more additional operations comprises generation of an alarm.

11. The medical implant of claim 10, wherein:
the medical implant is a cochlear implant;
the alarm is an electrical stimulation signal representing a specific audio signal; and
the electrical stimulation signal is delivered to a recipient of the medical implant.

12. The medical implant of claim 10, wherein the hermeticity failure sensor is configured to trigger the generation of the alarm only after a prescribed time delay has elapsed.

13. The medical implant of claim 10, wherein the hermeticity failure sensor comprises a first hermeticity failure sensor and a second, different hermeticity failure sensor.

14. An operational method of a medical implant having a hermetically sealed housing, the method comprising:
detecting a failure in hermeticity of the housing based on a change in volume and at least one of a change in brightness, sound, pressure, and atmospheric composition in the housing and acceleration to which the medical implant is subjected; and
triggering, following a failure detection, one or more operations.

15. The method of claim 14, wherein the medical implant comprises an implantable power source electrically connected to one or more other electrical components, and wherein triggering, following the failure detection, one or more operations comprises:
triggering an electrical disconnection of the implantable power source from the one or more other electrical components.

16. The method of claim 14, wherein triggering, following the failure detection, one or more operations comprises:
triggering a generation of an alarm.

17. The method of claim 14, wherein detecting a failure in the hermeticity of the housing comprises:
detecting a pressure change in the housing.

18. The method of claim 14, wherein detecting a failure in the hermeticity of the housing comprises:
directly detecting a change in humidity or surface moisture in the housing.

19. The method of claim 14, wherein detecting a failure in the hermeticity of the housing comprises:
detecting a shock applied to the housing.

20. The method of claim 14, wherein detecting a failure in the hermeticity of the housing comprises:
detecting volumetric changes in the housing resulting from ingress of fluid.

21. The medical implant of claim 1, wherein the hermeticity failure sensor comprises a differential pressure sensor.

22. The medical implant of claim 21, wherein the differential pressure sensor is configured to detect a pressure difference between two or more hermetically sealed chambers within the housing.

23. The medical implant of claim 21, wherein the differential pressure sensor is a strain gauge.

24. The medical implant of claim 8, wherein the light sensor comprises one or more diodes configured to detect a change in brightness in the housing.

25. A medical implant, comprising:
a hermetically sealed housing;
at least one component contained in the housing and vulnerable to hermeticity failure of the housing; and
a hermeticity failure sensor contained in the housing and configured to:
detect a failure in hermeticity of the housing based on a change in brightness within the housing and at least one of a change in sound, pressure, volume, and atmospheric composition in the housing and acceleration to which the medical implant is subjected; and
following a failure detection, trigger one or more additional operations.

* * * * *

UNITED STATES PATENT AND TRADEMARK OFFICE
CERTIFICATE OF CORRECTION

PATENT NO. : 8,634,918 B2
APPLICATION NO. : 13/123684
DATED : January 21, 2014
INVENTOR(S) : John Chambers It is certified that error appears in the above-identified patent and that said Letters Patent is hereby corrected as shown below:

On the title page item (73) Assignee, please correct:

From "Cochlear Limited, Macquarle University, NSW (AU)"

To "Cochlear Limited, Macquarie University, NSW (AU)".

Signed and Sealed this
Twenty-ninth Day of April, 2014

Michelle K. Lee
*Deputy Director of the United States Patent and Trademark Office*